United States Patent [19]

Ramacci

[11] 4,315,944

[45] Feb. 16, 1982

[54] PHARMACEUTICAL COMPOSITION COMPRISING L-CARNITINE FOR THE TREATMENT OF HYPERLIPIDAEMIAS AND HYPERLIPOPROTEINAEMIAS

[75] Inventor: Maria T. Ramacci, Rome, Italy

[73] Assignee: SIGMA-TAU Industrie Farmaceutiche Riunite S.p.A., Rome, Italy

[21] Appl. No.: 187,655

[22] Filed: Sep. 16, 1980

[30] Foreign Application Priority Data

Sep. 21, 1979 [IT] Italy .............................. 50331 A/79

[51] Int. Cl.³ .......................................... A61V 31/195
[52] U.S. Cl. .................................................... 424/319
[58] Field of Search ........................................ 424/319

[56] References Cited

U.S. PATENT DOCUMENTS 3,968,241  7/1976  De Felice ........................... 424/319

Primary Examiner—Stanley J. Friedman
Attorney, Agent, or Firm—Ladas & Parry

[57] ABSTRACT

In view of the discovery that D-carnitine exhibits an antagonistic effect versus the therapeutically adantageous effect of L-carnitine on free fatty acid levels, a pharmaceutical composition is described for the treatment of hyperlipidaemias and hyperlipoproteinaemias, characterized by the fact that all the carnitine present therein is solely L-carnitine.

3 Claims, 2 Drawing Figures

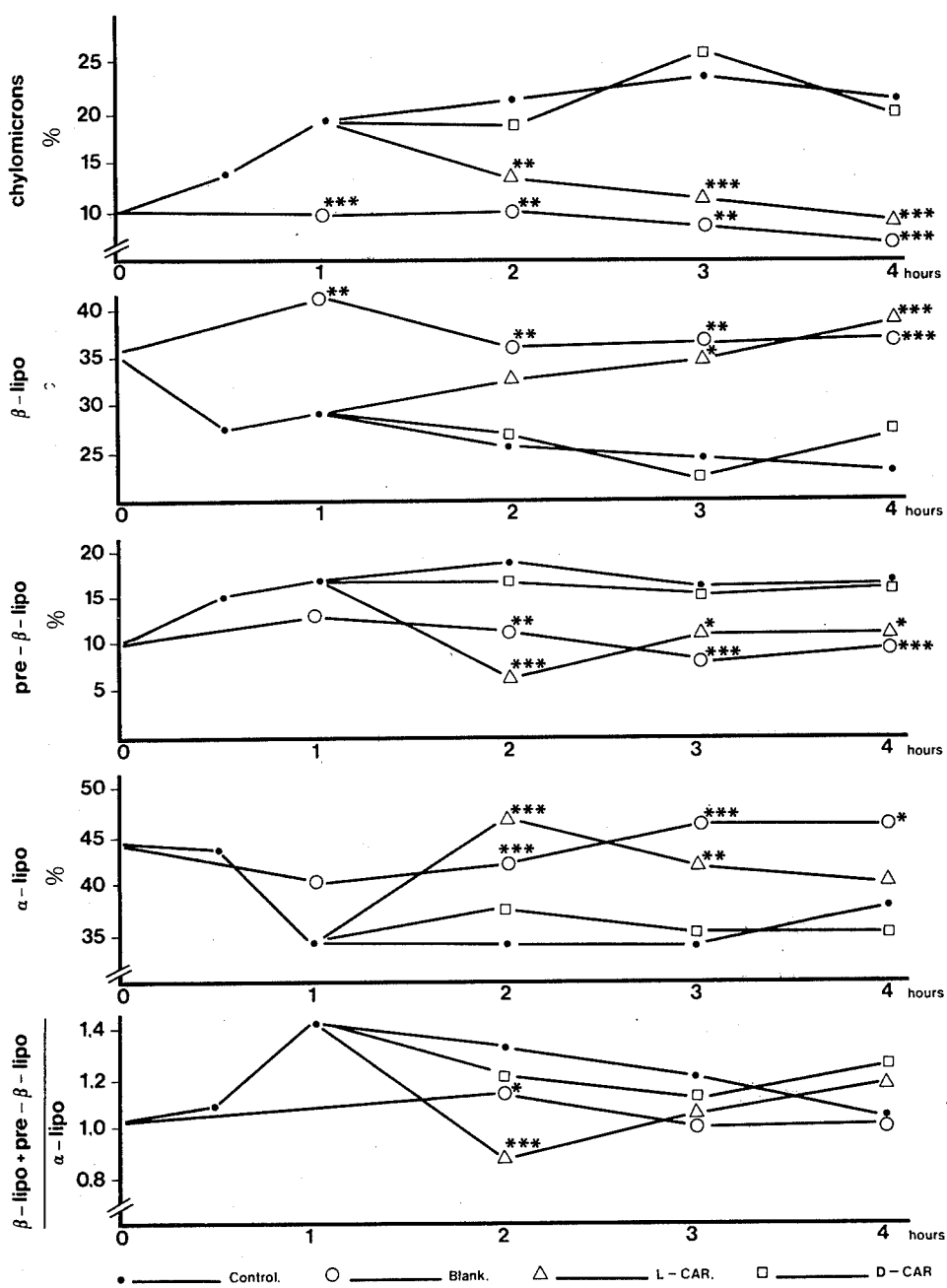
Fig. 1 Effect of L- and D-CAR on chylomicrons, $\beta$-lipo, $\alpha$-lipo, pre-$\beta$-lipo and on the ratio between $\beta$-lipo + pre-$\beta$-lipo and $\alpha$-lipo.
*, and * indicate P= 5%, 1% and 1‰ respectively, with respect to the control.
L-CAR = L-carnitine; D-CAR = D-carnitine

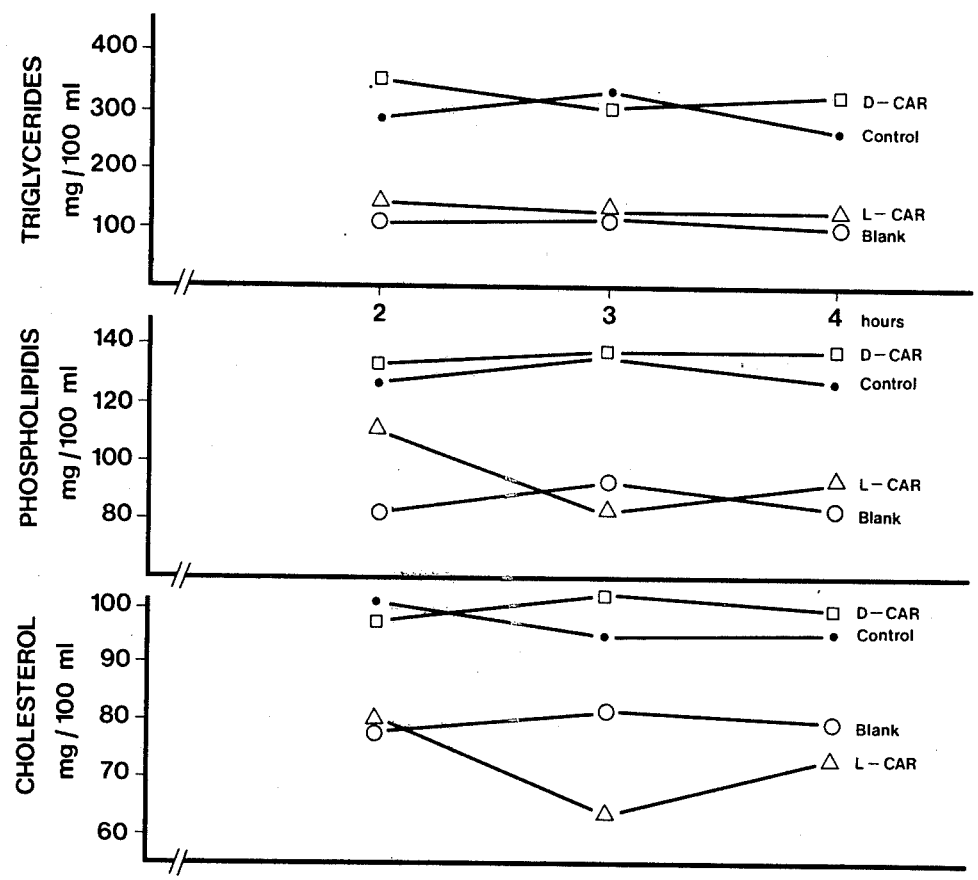
Fig. 2 Effect of L- and D-CAR on cholesterol, phospholipids and triglycerides in the oil-fed rat.
D-CAR = D-carnitine;   L-CAR = L-carnitine

PHARMACEUTICAL COMPOSITION COMPRISING L-CARNITINE FOR THE TREATMENT OF HYPERLIPIDAEMIAS AND HYPERLIPOPROTEINAEMIAS

The present invention pertains to a pharmaceutical composition comprising L-carnitine for the treatment of hyperlipidaemias and hyperlipiproteinaemias, and also to a therapeutical method comprising the administration of said composition.

The use in therapy of carnitine ($\beta$-hydroxy-$\gamma$-trimethylamino butyric acid) for the treatment of hyperlipidaemias and hyperlipoproteinaemias has already been described and claimed in the Italian patent applications nos. 47900 A/78 and 49353 A/78 filed by this same applicant on Feb. 3$^{rd}$ and May 15$^{th}$, 1978 respectively.

It is likewise known that carnitine presents an asymmetrical centre and therefore exists in the D and L stereoisomer forms. In the aforementioned Italian patent applications it is taught that either the racemate or the two individual isomers can be used indifferently. Although a certain preference can be given to the L form versus the D form in view of the known, slightly less toxicity of the L form versus the D form, the optical isomers D and L are both considered active in the above patent applications.

If it is considered moreover that, as is well known, the resolution of a racemate into the respective optical antipodes generally involves complex and expensive procedures, as in fact occurs in the case of the separation of L-carnitine from D-carnitine, the slight difference in toxicity does not suffice to justify, at least for the aforementioned therapeutical purposes, the use of separated optical antipodes, particularly of the L form, since it is economically more advantageous to use carnitine in its racemic form.

It has now been surprisingly found and is the presupposition of the present invention, that in the treatment of hyperlipoproteinaemias D-carnitine is not only slightly more toxic than L-carnitine, but indeed exhibits a true and proper antagonistic effect versus the therapeutically advantageous properties of L-carnitine, for instance on the lowering of the free fatty acid levels in the blood. It should be well understood that it has been discovered that the D form is not simply inactive compared to the L form, that is it does not act as a simple "diluent" of the active L form, but rather opposes the therapeutically advantageous effect of L-carnitine, at least partially blocking it.

Therefore the object of the present invention comprises a pharmaceutical composition for the treatment of hyperlipidaemias and hyperlipoproteinaemias comprising an effective amount of carnitine and by the fact that said carnitine is solely L-carnitine.

By the term "solely L-carnitine" it is meant, for the purposes of the present invention, not only that the component of the composition constituted by carnitine is substantially pure L-carnitine, thus disregarding eventual impurities or traces of D-carnitine, but also that carnitine, can be prevailingly L-carnitine, that is clearly exceeding the quantity of D-carnitine present, for instance by an L:D ratio of 95:5.

It has also been found that a particularly suitable pharmaceutical composition for the aforementioned therapeutical uses, when in the unit dosage form, comprises from approximately 50 to 500 mg of L-carnitine.

The scope of the present invention therefore also comprises a therapeutical method for the treatment of patients affected by hyperlipidaemias and hyperlipoproteinaemias, characterized by the fact of administering to said patients, via the oral or parenteral routes, a pharmaceutical composition comprising an effective amount of carnitine present solely in the L form.

Although the daily dose to be administered depends, using sound professional judgment, upon bodyweight, age, general conditions and the specific affection exhibited by the patient, it has been found that it is generally suitable to administer to said patients from approximately 2 to approximately 10 mg/kg of body weight/day of L-carnitine.

The antagonistic effect of D-carnitine versus L-carnitine has been experimentally demonstrated by means of the following techniques.

A - Effect of carnitine (DL, D and L) on the isolated rat liver

Male Wistar rats weighing 250±10 g maintained at normal feeding and caging conditions were anaesthetized with pentobarbital and the liver removed and after insertion of a canula perfused at the speed of 8 ml/min with free fatty acid (FFA) rich medium from the blood of 20-hour fasted rats.

DL carnitine, L-carnitine and D-carnitine were added respectively at the concentration of 0.5 mM/min equivalent to 80$\gamma$/8 ml/min or the vehicle in the case of the control group.

The uptake of FFA by the liver, considered expression of the metabolic activity of the organ was evaluated by measuring the FFA levels on the medium at various times during the experiment.

At the end of perfusion the concentration of liver phospholipids, trigycerides and cholesterol was also determined.

The values given in Table 1 indicate that after 20 min of infusion (the phenomenon follows a linear pattern from 0 to 20 min) L-carnitine determines a considerable reduction in the half-life of the initial FFA, while DL-carnitine and D-carnitine do not change the control group values.

The liver cholesterol and triglyceride values did not change, while the phospholipids resulted to be increased only by L-carnitine (Table 2).

In the perfused liver L-carnitine facilitates the uptake of FFA's and utilizes them for increasing the phospholipid pool. Conversely, D-carnitine does not exert any metabolic action and experimental data show that it antagonizes the carnitine present in the racemic mixture.

TABLE 1

Effect of DL-carnitine HCL, D-carnitine HCl and L-carnitine HCl (0.5 mMoles/minute) on the half-life of FFA in the perfusion medium of the isolated and perfused rat liver. Mean values ± SE calculated after 20 minutes of infusion with the compounds.

|  | after 20 minutes |
|---|---|
| Control | 20.92 ± 3.07 |
|  | (6) |
| DL-carnitine HCL | 19.00 ± 1.00 |
|  | (3) |
| D-carnitine HCL | 18.66 ± 7.17 |
|  | (3) |
| L-carnitine HCL | 12.33 ± 1.20 |

TABLE 1-continued

Effect of DL-carnitine HCL,
D-carnitine HCl and L-carnitine HCl (0.5 mMoles/minute)
on the half-life of FFA in the perfusion medium of the isolated
and perfused rat liver.
Mean values ± SE calculated after 20 minutes of infusion
with the compounds.

|  | after 20 minutes |
|---|---|
|  | (3) |

Number of tests in parenthesis.
Student's "t" tests for the differences versus the control.

TABLE 2

Effect of DL-carnitine HCL, D-carnitine HCL
and L-carnitine HCL (0.5 mMoles/min.) on tri-
glycerides and phospholipids of isolated and
perfused rat liver.
Mean % values ± SE after 120 minutes of
infusion with the compounds.

|  | Cholesterol % | Triglycerides % | Phospholipides % |
|---|---|---|---|
| Control | 0.229 ± 0.009 (6) | 1.309 ± 0.17 (6) | 2.519 ± 0.06 (6) |
| DL-carnitine HCL | 0.192 ± 0.016 (3) | 1.125 ± 0.15 (3) | 2.570 ± 0.41 (3) |
| D-carnitine HCL | 0.225 ± 0.017 (3) | 1.233 ± 0.30 (3) | 2.580 ± 0.26 (3) |
| L-carnitine HCL | 0.227 ± 0.005 (3) | 1.187 ± 0.11 (3) | 3.519 ± 0.16□ (3) |

Number of tests in parenthesis.
Student's "t" test for the differences versus the control.
□P = 5%.

B - Metabolic activity (in vivo)

Effect of one administration of carnitine (DL, D and L)
on free fatty acid (FFA) levels in the fasted rat Male Wistar rats weighing 190–220 g, maintained in groups of 5 under normal caging conditions and fasted for 17 hours with access only to water, were thus treated: 20 ml/kg per os of water, control group, and with 1g/kg per os of DL-carnitine, L-carnitine and D-carnitine respectively, the other groups.

1 hour after treatment the animals were sacrificed by decapitation and FFA was determined in serum using the Dole method.

In similar experimental conditions 20-hr fasted rats in groups of 5 were thus treated: the control group with physiological saline, and the other groups with DL, D and L-carnitine respectively at the dose of 250 mg/kg i.p. After 15 min following treatment the animals were sacrificed and FFA was determined in serum using the Dole method.

The results in Tables 3 and 4 show that DL-carnitine given at the dose of 1g/kg per os reduces the FFA levels by 13–15% Such levels increased in the rat after fasting. L-carnitine produces a 20–25% reduction while D-carnitine provokes a 6–9% increase versus control values.

The effect of reducing FFA provoked by L-carnitine is observed (−24%) also when the compound is given i.p. (Table 4).

In this experimental situation D-carnitine produces an increase (+34%) in FFA levels while DL carnitine shows poor activity. From this it is learnt that D-carnitine acts as an antagonist of the active laevorotatory form.

TABLE 3

Effect of DL-carnitine, L-carnitine and D-carnitine, 1 g/kg per
os, on serum FFA levels in the 17-hr fasted rat. % values versus
controls at 60 min. after treatment.

|  | FFA: control % | | |
|---|---|---|---|
|  | DL-carnitine | L-carnitine | D-carnitine |
| 1st experiment | −15 | −37 | +9 |
| 2nd experiment | −13 | −36 | +6 |

TABLE 4

Effect of DL-carnitine, L-carnitine, D-carnitine, 250 mg/kg i.p.,
on serum FFA levels of the 20-hr fasted rat.
Medium value ± SE at 15 min after treatment.

|  | FFA Eq/liter | | |
|---|---|---|---|
|  | Basal | +15 min. | % reduction |
| Physiological saline | 1190 ± 69 (27) | 1198 ± 54 (29) | unmeasurable |
| DL-carnitine | 987 ± 50 (10) | 931 ± 70 (10) | −6 |
| L-carnitine | 1350 ± 136 (5) | 1026 ± 147 (5) | −24 |
| D-carnitine | 1120 ± 167 (5) | 1412 ± 159 (5) | +34 |

C - Effect of carnitine (D and L) on
hyperlipoproteinaemia and hypertriglyceridaemia
induced by administering oil to the rat Male rats weighing 200±5 g, maintained in groups of 10 under normal caging and feeding conditions, were treated with triglycerideloads by oral administration of olive oil, 30 mg/kg, and 1 hour afterwards with D - and L-carnitine, 500 mg/kg per os.

The control animals received water. After 2,3 and 4 hours following oil administering sub-groups of animals were sacrificed. The serum percentage concentrations of chylomicrons, α, pre-β and β-lipoproteins by lipidogram, triglyceride, cholesterol and phospholipid serum levels and the serum content of free carnitine, acyl carnitine (short chain), and total carnitine were determined.

As shown in FIG. 1 the chylomicrons and pre-β-lipoproteins were markedly reduced and the α-lipoproteins were increased in the animals treated with L-carnitine.

Triglyceride and cholesterol levels were reduced (FIG. 2) and the formation of plasma acyl carnitine was increased. This effect was in no case present in the animals treated with D-carnitine, thus demonstrating the high selectivity of L-carnitine in the activities involving the mechanisms correlated to lipid metabolism, particularly lipoprotein metabolism.

CLINICAL CASES

Case 1

Male patient, 54 years of age, affected by primary hypertension; hypertriglyceridaemia accompanied by remarkably increased β-lipoproteins was ascertained upon hospitalization. Hypertension was treated with a diuretic only. When normal pressure was re-established, hyperlipidaemia was treated with L-carnitine 1 g per day in three 330-mg administrations. Prior to L-carnitine treatment the patient was given an appropriate isocaloric diet in the attempt to change the hyperlipidaemic pattern for the duration of the entire antihypertensive treatment, i.e. 29 days. The diet had moderately lowered triglyceride. Therefore the patient was defined as being resistant to the diet and L-carnitine treatment was commenced. Blood was sampled in basal conditions and on the 21st day. The decrease in triglyceride is evident and values are pratically normal. The $\beta/\alpha$-lipoprotein ratio is substantially normal.

|  | basal values | 21st day |
|---|---|---|
| triglyceride | 325 mg% | 180 mg% |
| cholesterol | 190 mg% | 160 mg% |
| pre-$\beta$-lipo | 52% | 37% |
| $\beta$-lipo | 31% | 43% |
| $\alpha$-lipo | 17% | 29.2% |

Case 2.

Female patient, 44 years of age, hospitalized for ischaemic heart disease and treated with nitro derivatives and a beta-blocker. The beta-blocker was suspended when ischaemia improved and trinitrin was given as required. Successively, since hyperlipidaemia was detected, L-carnitine treatment was initiated, 1 g per day in three 330-mg (approx.) administrations.

Blood samples were drawn in basal conditions, and after 3 weeks of treatment a considerable reduction in triglycerides and a decrease in the $\beta/\alpha$-lipoprotein ratio were observed.

|  | basal values | 21 days |
|---|---|---|
| triglyceride | 395 mg% | 205 mg% |
| cholesterol | 249 mg% | 219 mg% |
| pre-$\beta$-lipo | 52% | 37% |
| $\beta$-lipo | 32% | 41% |
| $\alpha$-lipo | 16% | 21% |

Case 3

Male diabetic patient, 55 years of age, hospitalized for sequelae of hemiplagia. Hypoglycaemizing agents were administered to the patient via the oral route until a return to normal glyceamia and therapy was continued at minimum doses. However, the lipid pattern was markedly pathological in spite of hypoglycaemizing and dietetic treatment. The decision was taken to start L-carnitine therapy at the regimen of 1.33 g daily in four 330-mg (approx.) administrations. Treatment was continued for 4 weeks and blood was analyzed in basal conditions and on the 28$^{th}$ day. Triglyceride and total cholesterol were remarkably lowered with a decreased $\beta/\alpha$-lipoprotein ratio at the end of therapy.

|  | basal values | 28 days |
|---|---|---|
| triglyceride | 228 mg% | 158 mg% |
| cholesterol | 267 mg% | 160 mg% |
| pre-$\beta$-lipo | 35% | 30% |
| $\beta$-lipo | 44% | 45% |
| $\alpha$-lipo | 21% | 25% |

Case 4

Female patient, 57 years of age. Obese patient due to erraneouse diet was hospitalized for investigation. She was put on a hypocaloric diet until normal bodyweight for her age and height was restored. Upon hospital admittance the lipid pattern was disordered: the triglycerides and cholesterol were above normal values. After the diet the lipid pattern showed a clear-cut deterioration and the triglycerides exhibited a further increase. The patient was given L-carnitine therapy at a daily dosage of 1 g in three 330-mg (approx.) administrations.

The patient continued therapy for 3 weeks and lipid values returned to nearly normal. The above case suggests the use of L-carnitine as a therapeutical aid in slimming diets in order to correct hypertriglyceridaemia probably due to lipid mobilization.

|  | basal values | 21 days |
|---|---|---|
| triglycerides | 409 mg% | 219 mg% |
| cholesterol | 313 mg% | 190 mg% |
| pre-$\beta$-lipo | 48% | 30% |
| $\beta$-lipo | 39% | 52% |
| $\alpha$-lipo | 13% | 18% |

Two examples pertaining to the tablet composition for the purposes of manufacture are given hereunder:

EXAMPLE 1

L-carnitine: 330 mg
magnesium stearate: 50 mg
microcrystalline cellulose: 24 mg

EXAMPLE 2

L-carnitine: 330 mg
stearic acid: 35 mg
microcristalline cellulose: 25 mg

What is claimed is:

1. A therapeutical method for the treatment of patients affected by hyperlipidaemias and hyperlipoproteinaemias characterized by the fact of administering to said patients, orally or parenterally, a pharmaceutical composition comprising an effective amount of carnitine present solely in the L form.

2. A therapeutical method for treating patients exhibiting an adnormally high value of the ratio between $\beta$-lipoproteins and $\alpha$-lipoproteins comprising administering to said patients of an effective amount of L-carnitine, sufficient to restore said ratio to normal values.

3. The therapeutical method according to claim 1 or 2, characterized by the fact of administering to said patients from approximately 2 mg/kg to approximately 10 mg/kg of bodyweight per day of L-carnitine.

* * * * *